United States Patent [19]

Aldcroft et al.

[11] Patent Number: 5,624,652
[45] Date of Patent: Apr. 29, 1997

[54] SILICAS

[75] Inventors: Derek Aldcroft, South Wirral; Peter W. Stanier, Cheshire, both of United Kingdom

[73] Assignee: Crosfield Limited, Warrington, United Kingdom

[21] Appl. No.: 424,453

[22] PCT Filed: Oct. 26, 1993

[86] PCT No.: PCT/EP93/03006

§ 371 Date: Jun. 1, 1995

§ 102(e) Date: Jun. 1, 1995

[87] PCT Pub. No.: WO94/10087

PCT Pub. Date: May 11, 1994

[30] Foreign Application Priority Data

Oct. 28, 1992 [EP] European Pat. Off. ............ 92309858

[51] Int. Cl.⁶ ................ C01B 33/12; C09C 1/68
[52] U.S. Cl. ................ 423/335; 423/339; 51/308; 51/309
[58] Field of Search .................. 423/335, 339; 51/308, 309

[56] References Cited

U.S. PATENT DOCUMENTS

| | | | |
|---|---|---|---|
| 4,015,996 | 4/1977 | Wason | 423/339 |
| 4,040,858 | 8/1977 | Wason | 423/339 |
| 4,122,160 | 10/1978 | Wason | 423/335 |
| 4,312,845 | 1/1982 | Wason | 423/339 |
| 4,420,312 | 12/1983 | Wason | 423/339 |
| 4,581,217 | 4/1986 | Shinpo et al. | 423/339 |
| 4,857,289 | 8/1989 | Nauroth et al. | 423/339 |
| 4,956,167 | 9/1990 | Aldcroft et al. | 423/339 |
| 4,992,251 | 2/1991 | Aldcroft et al. | 423/335 |
| 5,098,695 | 3/1992 | Newton et al. | 423/335 |
| 5,225,177 | 7/1993 | Wason et al. | 423/339 |
| 5,447,704 | 9/1995 | Aldcroft et al. | 423/339 |
| 5,484,581 | 1/1996 | Esch et al. | 423/335 |
| 5,512,271 | 4/1996 | McKeown et al. | 423/339 |

FOREIGN PATENT DOCUMENTS

| | | | |
|---|---|---|---|
| 0139754 | 5/1985 | European Pat. Off. | A61K 7/16 |
| 0227334 | 7/1987 | European Pat. Off. | C01B 33/18 |

*Primary Examiner*—Mark L. Bell
*Assistant Examiner*—Louis M. Troilo
*Attorney, Agent, or Firm*—Cushman Darby & Cushman IP Group Pillsbury Madison & Sutro LLP

[57] ABSTRACT

Amorphous silicas suitable for use as abrasives in transparent toothpastes can be prepared by a precipitation route. These silicas are distinguished by having a BET surface area of 10 to 90 $M^2/g$, a weight mean particle size of 5 to 15 micron, and a plastics abrasion value of 16 to 20, a transmission of at least 70% in the RI range from 1.430 to 1.443 and an oil absorbtion in the range from about 70 to about 150 $cm^3/100$ g.

3 Claims, No Drawings

SILICAS

FIELD ON THE INVENTION

This invention relates to synthetic amorphous silicas, especially precipitated silicas, of use, for example, as abrasive agents in transparent toothpaste compositions.

BACKGROUND OF THE INVENTION

Toothpaste compositions are well characterised in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients. Of these components the abrasive agent is required to provide the appropriate cleaning and plaque removal without subjecting the tooth itself to excessive abrasion. Typically a toothpaste composition will contain from about 5% to about 50% preferably up to about 30% by weight of abrasive.

Commonly used abrasives are aluminas, calcium carbonates and calcium phosphates. More recently synthetic silicas have been adopted because of their efficient cleaning, compatibitity with other ingredients and their physical properties. An important property of a silica for use in transparent toothpaste formulations is its apparent refractive index, and the lower this value in the chosen water/humectant system the more water can be allowed for by the formulator in the transparent dentifrice. This replacement of the more expensive humectant e.g. Sorbitol and/or Glycerol, by water leads to substantial economic benefits to the formulator.

The inventors have shown that the apparent refractive index of an amorphous silica can be controlled by the careful selection of process conditions at the precipitation stage of the preparation of the silica. It can be demonstrated that changing such conditions as pH, electrolyte level and silica concentration alters the fundamental features of the overall pore size distribution present in the amorphous silica. Amorphous silicas can be prepared with an extremely broad pore size distribution stretching from ultramicropores (below 0.7 nm), through supermicropores (0.7 to 2 nm), continuing to mesopores (2 nm to 50 nm), finally macropores (above 50 nm), in accordance with the classification given in, Characterisation of Porous Solids; An Introductory Survey by K. W. S. Sing in Characterisation of Porous Solids II 1991 Elsevier Science Publishers BV Amsterdam.

It is postulated that the level of ultramicropores, which are defined as pores small enough to exclude the nitrogen molecule, controls the degree of movement in the apparent refractive index of the amorphous silica when it is brought into contact with the water/humectant system. As the number of ultramicropores increases, there will be a higher propensity to preferentially adsorb water from the water/humectant system and hence lower the apparent refractive index of the silica.

Surprisingly, silicas of the invention retain their ultramicropore distribution when subjected to ageing and therefore retain their apparent refractive index position. Additionally, the silicas retain good clarity making them suitable for use in transparent toothpaste formulations.

The inventors have shown, by careful selection of process conditions, followed by controlled subsequent ageing, amorphous silicas can be prepared with extremely low surface areas (below 100 $m^2g^{-1}$), having a low apparent refractive index of approximately 1.44, but maintaining medium to high abrasivity and excellent clarity when the silica is dispersed in a water/humectant system.

PRIOR ART

The use of precipitated silicas with low to medium structure as abrasives in toothpaste formulations can be found in GB 1482354 and GB 1482355 (Huber), EP-A-0227334 and EP-A-0236070 (Unilever), EP-A-0143848 and EP-A-0139754 (Taki). GB 1482354 and GB 1482355 disclose silicas for use in toothpastes in general but are silent on the possible application in transparent toothpastes. EP-A-0227334 and EP-A-0236070 state the silicas as defined, even those having a surface area of below 100 $m^2g^{-1}$, that are produced from precursors which age relatively rapidly can have lower apparent refractive index but their clarity remains poor. It is disclosed in EP-A-0236070 that the silicas are only suited for formulating into opaque toothpastes, whilst the silicas of EP-A-0227334 can also be used in translucent formulations.

EP-A-0143848 and EP-A-0139754 describe silicas with a texture and refractive index more suited to transparent toothpastes. The documents disclose a process for the preparation of amorphous silicas with apparent refractive indices in the range 1.42 to 1.47 which on firing at 1100° C. yield a phase which is amorphous to x-rays, having B.E.T. surface areas in specified ranges, EP-A-0143848, 270 to 500 $m^2g^{-1}$, and EP-A-0139754:45 to 60 $m^2g^{-1}$, respectively. The lower surface area variant is also described as having excellent clarity in the toothpaste formulation with an apparent refractive index of approximately 1.44, and it is shown later to have low perspex abrasion values (below 10) and high oil absorption (above 160 $cm^3$/100 g).

GENERAL DESCRIPTION OF THE INVENTION

When incorporated into a dentifrice formulation, the amorphous precipitated silicas of the invention, having a surface area less than 100 $m^2g^{-1}$, provide a novel range of properties, combining high levels of abrasivity with good transparency at low apparent refractive index of approximately 1.44. The levels of abrasivity obtained with the silicas are usually high in view of the levels of openness of the structure the silicas possess as defined by oil absorption and porosity measurements. In particular, such high levels of abrasivity coupled with good dentifrice transparency at low refractive index have not been obtained previously with low surface area precipitated silicas.

The silicas of the invention are capable of providing high levels of abrasion even at relatively low particle size (i.e. 5 to 10 micron) even if the particle size distribution is controlled to eliminate coarse particles, particularly those greater than 30 μm. It is accepted the abrasivity of an amorphous silica can be increased by broadening the weight particle size distribution to include larger percentages of particles in excess of 20 μm. However, it must be recognized that these materials can give rise to unacceptable mouth feel when formulated into toothpastes.

The silicas can be prepared with low levels of cations, e.g. calcium and magnesium, by washing the filter cake, the precursor to the dried product, with de-ionised water such that the subsequently dried product gives extra stability when formulated into a toothpaste containing fluoride ions.

In general the characterisation of amorphous silicas containing such a broad spectrum of pore sizes (below 0.7 nm to above 60 nm) by nitrogen adsorption is not meaningful because the nitrogen molecule is excluded from the pores with diameter below 0.7 nm, whilst those with a diameter above 60 nm cannot be distinguished from saturation of nitrogen at the surface. To measure the total porosity present in pore diameters above 4 nm it is necessary to employ alternative procedures such as oil absorption and mercury porosimetry. Helium pycnometry can be utilised to show the presence of ultramicropores and supermicropores will be detected by nitrogen adsorption. The extent to which pores with a diameter less than 0.7 nm dominate the micropore size distribution is shown by the shift in the apparent refractive index of the amorphous precipitated silica when it is in contact with the humectant/water system.

Accordingly it is a first object of the present invention to provide an amorphous silica, preferably a precipitated silica having (i) a B.E.T. surface area in the range from about 10 to about 90 $m^2g^{-1}$, (ii) a weight mean particle size in the range from about 5 to about 15 microns, with less than 15%, preferably less than 10% of the weight particle size distribution greater than 20 microns and less than 5% greater than 25 microns, (iii) a plastics abrasion value in the range from about 16, preferably about 20, to about 26 (iv) a transmission of at least about 70%, preferably at least 80%, in the refractive index range of 1.430 to 1.443, (v) an oil absorption in the range from about 70 to about 150.

After firing at 1100° C. the silicas of the invention have a crystal structure of alpha cristobalite.

Usually the moisture content of the silica will be less than about 25%, preferably less than about 15% w/w.

It is a second object of the present invention to provide a process for the preparation of an amorphous precipitated silica having (i) a B.E.T. surface area in the range from about 10 to about 90 $m^2g^{-1}$, (ii) a weight mean particle size in the range from about 5 to about 15 microns, with less than 15%, preferably less than 10% of the weight particle size distribution greater than 20 microns and less than 5% greater than 25 microns (iii) a plastics abrasion value in the range from about 16 to about 26 (iv) a transmission of at least about 70% in the refractive index range of 1.430 to 1.443 (v) an oil absorption in the range from about 70 to about 150, by reacting an alkali (M) metal silicate solution with ratio $SiO_2$:$M_2O$ in the range 3.0 to 3.5, in the presence of an electrolyte, preferably sodium chloride, where the ratio of NaCl $SiO_2$ is between 1:12 and 1:4, preferably between 1:10 and 1:4, with a mineral acid such that the pH is in the range from about 8.5, preferably 9.0, to about 10.0, and the silica concentration at the end of the primary acid addition is from about 6.0 to about 8.0 w/w, at a temperature from about 80°, preferably 90°, to about 100° C., ageing this slurry for about 10 to 50 minutes, adding a secondary amount of dilute mineral acid until the pH is in the range 2 to 5 to ensure complete neutralisation of the alkali containing silica solution, filtering, washing and drying the product obtained.

It is a third object of the present invention to provide a transparent toothpaste composition which contains from about 5% to about 50% by weight, preferably up to about 30% of an amorphous precipitated silica of the invention.

STANDARD PROCEDURES

The silicas of the invention are defined in terms of their physical and chemical properties. The standard test methods used for these properties are:

i) Surface Area:

Surface area is determined using standard nitrogen adsorption methods of Brunauer, Emmett and Teller (BET), using a single point method with a Sorpty 1750 apparatus supplied by Carlo Erba Company of Italy. The sample was outgassed under vacuum at 270° C. for 1 hour before measurement.

ii) Oil Absorption:

The oil absorption is determined by the ASTM spatula rub-out method (American Society of Test Material Standards, D, 281).

The test is based upon the principle of mixing linseed oil with a silica by rubbing with a spatula on a smooth surface until a stiff putty-like paste is formed which will not break or separate when it is cut with the spatula. The volume of oil used is then put into the following equation;

$$\text{Oil absorption} = \frac{cm^3 \text{ oil absorption} \times 100}{\text{wt. of silica sample in g}}$$

$$= cm^3 \text{ oil/100 g silica}$$

iii) Weight Mean Particle Size:

The weight mean particle size of the silicas is determined with the aid of a Malvern Mastersizer, using a 45 mm lens. This instrument, made by Malvern Instruments, Malvern, Worcestershire uses the principle of Fraunhöffer diffraction utilizing a low power He/Ne laser. Before measurement the sample is dispersed ultrasonically in water for a period of 7 minutes to form an aqueous suspension.

The Malvern Particle Sizer measures the weight particle size distribution of the silica. The weight mean particle size ($d_{50}$) or 50 percentile, the 10 percentile ($d_{10}$) and the 90 percentile ($d_{90}$) are easily obtained from the data generated by the instrument.

iv) Plastics Abrasion Value (PAV):

This test is based upon a toothbrush head brushing a Perspex plate in contact with a suspension of the silica in a sorbitol/glycerol mixture. Normally the slurry composition is as follows:

| | |
|---|---|
| Silica | 2.5 grams |
| Glycerol | 10.0 grams |
| Sorbitol Syrup* | 23.0 grams |

*Syrup contains 70% sorbitol/30% water

All components are weighed into a beaker and dispersed for 2 minutes at 1500 rpm using a simple stirrer. A 110 mm×55 mm×3 mm sheet of standard 'Perspex' Clear Cast Acrylic sheet grade 000, manufactured by Imperial Chemical Industries Ltd, is used for the test.

The test is carried out using a modified Wet Abrasion Scrub Tester produced by Sheen Instruments, 8 Waldegrave Road, Teddington, Middlesex, TW11 8LD. The modification is to change the holder so that a toothbrush can be used instead of a paint brush. In addition a weight of 400 g is attached to the brush assembly, which weighs 145 g, to force the brush onto the Perspex plate. The toothbrush has a multi-tufted, flat trim nylon head with round ended filaments and medium texture for example as the one sold under the trade name Wisdom manufactured by Addis Ltd, Harford, England.

A Galvanometer is calibrated using a 45° Plaspec gloss head detector and a standard (50% gloss) reflecting plate. The Galvanometer reading is adjusted to a value of 50 under these conditions. The reading of the fresh Perspex plate is then carried out using the same reflectance arrangement.

The fresh piece of Perspex is then fitted into a holder. Two $cm^3$ of the dispersed silica, sufficient to lubricate fully the brushing stroke, is placed on the plate and the brush head lowered onto the plate. The machine is switched on and the plate subjected to three hundred strokes of the weighted brush head. The plate is removed from the holder and all the suspension is washed off. It is then dried and re-measured for its gloss value. The abrasion value is the difference between the unabraded value and the value after abrasion.

This test procedure, when applied to known abrasives, gave the following typical values:

|  | Plastics Abrasion Value |
|---|---|
| Calcium carbonate (15 micron) | 32 |
| Silica xerogel (10 micron) prepared by UK 1264292 method | 25 |
| Alumina trihydrate (Gibbsite) (15 micron) | 16 |
| Calcium pyrophosphate (10 micron) | 14 |
| Dicalcium phosphate dihydrate (15 micron) | 7 | v) Electrolyte Levels:

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

vi) Moisture Loss at 105° C.:

Moisture loss is determined by the loss in weight of a silica when dried to constant weight in an electric oven at 105° C.

vii) Ignition Loss as 1000° C.:

Ignition loss is determined by the loss in weight of a silica when ignited in a furnace at 1000° C. to constant weight.

viii) pH:

This measurement is carried out on a 5% w/w suspension of the silica in boiled demineralised water ($CO_2$ free).

ix) Crystal Form After Firing at 1100° C.:

A sample of the silica is fired in an electric muffle furnace for one hour at 1100° C. The treated sample is allowed to cool and the crystal structure present identified from the trace obtained from an x-ray diffractometer.

x) Mercury Intrusion Volume:

Mercury intrusion volume are determined (in $cm^3/g$) by standard mercury intrusion procedures using a Micromeritics Autopore 9220 mercury porosimeter. The pore radius is calculated from the Washburn equation using values of surface tension for mercury of 485 dynes/cm and contact angle of 140°.

Prior to measurement the sample was outgassed at room temperature to a pressure of 50 microns of mercury. The mercury intrusion volume recorded is that at which the intra-particle pore volume is taken as less than 1.0 micron.

xi) Refractive Index (RI)/transmission:

The sample of silica is dispersed in a range of Sorbitol syrup (70% Sorbitol)/water mixtures. After de-aeration, usually 1 hour, the transmission of the dispersions is determined using a spectrophotometer at 589 nm; water being used as blank. The refractive index of each dispersion is also measured using an Abbe refractometer.

A graphical representation of transmission plotted against refractive index allows the range of refractive indices over which the transmission exceeds 70% to be determined. The maximum transmission of the sample and the refractive index at which this is obtained can also be estimated from this graph.

xii) Skeletal Density Using Helium Pycnometry:

The skeletal density of silica samples is determined using a Micromeretics Accupyc 1330 helium pycnometer. Before measuring the samples the instrument is calibrated with helium. Sufficient measurements (usually three) are carried out to allow an accurate calculation of the chamber volume and "dead space" in the apparatus.

Measurement of the samples is a repeat of the calibration routine but first the samples are dried at 120° C. for two hours prior to analysis. The calibrated empty volume of the pycnometer has been determined. For each analysis a sample of known weight is placed in the chamber and the measurement is made automatically.

REFERENCE EXAMPLES 1 TO 3

In order to emphasize the characteristic features of the invention, the following reference examples are given to differentiate from the current invention.

A heated stirred reaction vessel was used for silicate/acid reaction as described below:

Mixing is an important feature in the reaction of silicate and sulphuric acid. Consequently fixed specifications as listed in Chemineer Inc. Chem. Eng. April 26th (1976) pages 102–110, have been used to design the baffled heated stirred reaction vessels. Whilst the turbine design is optional to the mixing geometry, a 6-bladed 30° pitched bladed unit has been chosen for our experiments in order to ensure maximum mixing effectiveness with minium shear. Shear has been supplied to the reaction mixture by circulating the contents of the reaction vessel through an external high shear mixer (Silverson), containing a square hole high shear screen, throughout the simultaneous addition of silicate and acid, or in the case of reference example 3, throughout the addition of acid. The energy input being commensurate with the volume flow and number of recirculations required as specified by the manufacturer.

The solutions used in the process were as follows:

i) Sodium silicate solutions have a $SiO_2:NaO_2$ ratio in the range of 3.2 to 3.4:1.

ii) A sulphuric acid solution of specific gravity 1.06 (10.0% w/w solution) to 1.15 (21.4% w/w solution).

iii) An electrolyte solution as defined in each preparation.

The following procedure was adopted in the preparation of the precipitated silicas. Values of reactant concentrations, volumes and temperatures are given in Table 1.

(A) liters of water were placed in the vessel with (B) liters of electrolyte solution and (C) liters of the sodium silicate solution. This mixture was then stirred and heated to (E) °C.

For simultaneous addition routes (reference examples 1 and 2), the sodium silicate ((D) liters) and sulphuric acid ((F) liters) solutions were then added simultaneously over a period of about (G) minutes with stirring while maintaining the temperature at (E) °C. The flow rates of the silicate and acid solutions were uniform throughout the addition period to ensure that a constant pH, in the range from about 8.5 to about 10.5, was maintained in the vessel.

In the case of reference example 3, where all the silicate was present at the start of the reaction, (F) liters of sulphuric acid was added over a period of (G) minutes to give a pH of 10.5.

In all examples sulphuric solution (II) was then added over a period of (K) minutes with continued mixing, (but without Silverson shear), to reduce the pH of the slurry to the range of 2.5 to 5.0. During this addition (II) of acid, the temperature was maintained at (E) °C.

The resultant slurry was then filtered, washed with water to remove excess electrolyte and flash dried.

The precipitated silicas obtained had the properties, expressed on a dry weight basis listed in Table 2.

It can be seen that it is possible to prepare amorphous precipitated silicas with medium to high abrasivity (PAV 16–25), lower apparent refractive index, and good transparency, but if the freshly precipitated silica slurry is not aged the surface area of the dried product is 250 to 350 $m^2g^{-1}$.

SPECIFIC DESCRIPTION OF THE INVENTION

Examples of the preparation of precipitated silicas will now be given to illustrate but not limit the invention.

EXAMPLE 1–6

The procedures outlined in References 1–3 have been followed for the prepared silicas but in these examples of the invention, an ageing step of (H) minutes has been introduced after the primary addition of reactants. Additionally, examples 4 and 5 did not have external shear from a Silverson mixer and both preparations utilised solid sodium chloride added to the water pool and allowed to dissolve before primary addition of reactants.

Reaction conditions and the properties of the dried products are listed in Tables III and IV respectively.

As a consequence of the ageing step the silicas of the invention have low surface areas, but they still have high transmission at low apparent refractive index and medium to high abrasion levels.

The process is shown to be controlled by such process parameters as sol ageing, silica concentration, electrolyte concentration and solution pH.

ADDITIONAL REFERENCES

The most relevant prior art is given in the Taki patent EPA 0139754, and to distinguish the silicas of this invention from the present one, Examples 1, 2 and 3 as listed in EP-A-0139754 have been repeated. It must be emphasised the repetitions are the examples of the Taki invention and not the Taki reference type. All the variables highlighted as being important have been followed, as closely as a person skilled in the art can achieve, according to the teachings of the patent.

Table V lists the properties of the silicas of the repetitions together with typical examples of the present invention. It can be seen that the amorphous silicas of the prepared examples from Taki have low plastics abrasion values (below 10) and high oil absorption (above 150 cm³/100 g). In accordance with the teachings of the invention the silicas yielded a phase amorphous to x-rays after firing at 1100° C., had low surface area and low refractive index.

EXAMPLE 7

The amorphous silicas of the invention provided satisfactory toothpastes in which they were incorporated. The toothpastes have commercially acceptable properties for stability and usage. A typical formulation using a silica of this invention is given in Table VI.

TABLE I

|  | TEST NO. | | |
| --- | --- | --- | --- |
|  | REF. 1 | REF. 2 | REF. 3 |
| Vessel Capacity (Liters) | 64 | 64 | 64 |
| Water Volume (A) (Liters) | 18.0 | 13.1 | 12.6 |
| Electrolyte Used | NaCl | NaCl | NaCl |
| Concn. of Electrolyte (B) (% w/w) | 25 | 25 | 25 |
| Vol. of Electrolyte (B) (Liters) | 1.7 | 0.9 | 2.4 |
| Silicate Ratio $SiO_2/Na_2O$ By Weight | 3.30 | 3.29 | 3.26 |
| $SiO_2$ Concn. in Sodium Silicate (% w/w) | 17.49 | 16.52 | 17.41 |
| Silicate Vol. (C) (Liters) | 0.1 | 0.1 | 10.4 |
| Silicate Vol. (D) (Liters) | 14.2 | 11.4 | 0 |
| Acid Concn. (% w/w/) | 18.5 | 18.1 | 18.0 |
| Acid Vol (Liters) (F) | 7.6 | 5.7 | 5.4 |
| Temperature (E) (°C.) | 80 | 98 | 98 |
| Acid I Addition Time (G) (Mins) | 20 | 40 | 20 |
| Acid II Addition Time (K) (Mins) | 10 | 10 | 10 |

TABLE II

|  | TEST NO. | | |
| --- | --- | --- | --- |
|  | REF. 1 | REF. 2 | REF. 3 |
| Surface Area ($m^2g^{-1}$) | 307 | 262 | 336 |
| Plastics Abrasion Value | 16 | 20 | 16 |
| Maximum % Transmission | 77 | 78 | 71 |
| At Refractive Index of | 1.440 | 1.440 | 1.438 |
| Form after Firing @ 1100° C.* | Ac. | Ac. | Ac. |
| Mercury Intrusion Vol. ($cm^3g^{-1}$) | 0.46 | 0.45 | 0.81 |
| Ignition Loss @ 1000° C. (%) | 10.0 | 7.0 | 8.2 |
| Moisture Loss @ 105° C. (%) | 5.1 | 2.8 | 3.2 |
| pH | 7.5 | 6.3 | 7.3 |
| Electrolyte Level $So^-4$ (%) | 0.05 | 0.11 | 0.05 |
| Electrolyte Level $Cl^-$ (%) | 0.06 | 0.06 | 0.01 |
| Oil Absorption ($cm^3$/100 g) | 120 | 110 | 110 |
| Particle Size Distribution (Micron) |  |  |  |
| 10 Percentile | 3.3 | 3.5 | 2.7 |
| 50 Percentile | 7.8 | 7.2 | 11.5 |
| 90 Percentile | 12.0 | 12.5 | 18.0 |
| % Greater than 20 micron | 7.0 | 2.0 | 9.0 |
| % Greater than 25 micron | <2.0 | <1.0 | 4.6 |
| Helium Density (g $cm^{-3}$) | 2.0346 | 2.0836 | 2.0448 |

*Ac. indicates alpha-cristobalite

TABLE III

|  | TEST NO. | | | | | |
| --- | --- | --- | --- | --- | --- | --- |
|  | 1 | 2 | 3 | 4 | 5 | 6 |
| Vessel Capacity (Liters) | 300 | 64 | 64 | 64 | 64 | 300 |
| Water Volume (A) (Liters) | 64.4 | 8.9 | 12.8 | 14.4 | 10.6 | 71.4 |
| Electrolyte used | NaCl | NaCl | NaCl | NaCl | NaCl | NaCl |
| Concn. of Electrolyte (% w/w) | 25 | 25 | 25 | 100 | 100 | 25 |

TABLE III-continued

|  | TEST NO. | | | | | |
| --- | --- | --- | --- | --- | --- | --- |
|  | 1 | 2 | 3 | 4 | 5 | 6 |
| Vol. of Electrolyte (B) (Liters) | 4.8 | 0.95 | 1.3 | — | — | 5.1 |
| Wt. of Electrolyte (B) (gms) | — | — | — | 438 | 313 | — |
| Silicate Ratio $SiO_2/Na_2O$ By Weight | 3.29 | 3.36 | 3.30 | 3.23 | 3.23 | 3.29 |
| $SiO_2$ Concn. in Sodium Silicate (% w/w) | 16.4 | 17.3 | 17.4 | 16.7 | 16.7 | 16.6 |
| Silicate Vol. (C) (Liters) | 0.6 | 0.1 | 0.1 | 0.1 | 0.1 | 0.6 |
| Silicate Vol. (D) (Liters) | 62 | 10.8 | 10.7 | 10.8 | 13.1 | 61 |
| Acid Concn. (% w/w) | 17.2 | 10.0 | 17.3 | 17.5 | 10.0 | 17.5 |
| Acid Vol. (F) (Liters) | 40 | 9.0 | 4.9 | 4.7 | 11.2 | 33.4 |
| Temperature (E) (°C.) | 97 | 98 | 98 | 98 | 98 | 97 |
| Acid I Addition Time (G) (Mins) | 20 | 20 | 20 | 20 | 20 | 20 |
| Acid II Addition Time (K) (Mins) | 10 | 10 | 10 | 8 | 10 | 12 |
| Age Time (H) (Mins) | 30 | 10 | 10 | 10 | 10 | 10 |

TABLE IV

|  | TEST NO. | | | | | |
| --- | --- | --- | --- | --- | --- | --- |
|  | 1 | 2 | 3 | 4 | 5 | 6 |
| Surface Area ($m^2g^{-1}$) | 40 | 86 | 62 | 41 | 76 | 33 |
| Plastics Abrasion Value | 24 | 16 | 17 | 16 | 21 | 26 |
| Max. % Transmission | 75 | 77 | 84 | 87 | 79 | 83 |
| At Refractive Index of | 1.441 | 1.439 | 1.443 | 1.440 | 1.439 | 1.442 |
| Form after firing @ 1100° C.* | Ac | Ac | Ac | Ac | Ac | Ac |
| Mercury Intrusion Vol. ($cm^3g^{-1}$) | NM | 0.44 | 0.44 | 0.65 | 0.53 | 0.41 |
| Ignition Loss @ 1000° C. | 8.2 | 7.1 | 6.6 | 7.0 | 6.3 | 9.6 |
| Moisture Loss @ 105° C. | 2.0 | 2.5 | 1.2 | 1.0 | 1.7 | 5.4 |
| pH | 6.4 | 6.1 | 7.5 | 6.1 | 6.4 | 7.0 |
| Electrolyte Level $SO^=4$ (%) | 0.25 | 0.05 | 0.03 | 0.04 | 0.05 | 0.06 |
| Electrolyte Level $Cl^-$ (%) | 0.18 | 0.01 | 0.02 | 0.04 | 0.03 | 0.01 |
| Oil Absorption ($cm^3/100$ g) | 125 | 90 | 100 | 105 | 90 | 130 |
| Particle Size Distribution (Microns) | | | | | | |
| 10 Percentile | 3.1 | 2.2 | 2.4 | 2.2 | 1.9 | 2.4 |
| 50 Percentile | 8.3 | 7.2 | 6.2 | 7.7 | 6.5 | 7.8 |
| 90 Percentile | 11.0 | 13.0 | 13.4 | 15.7 | 16.4 | 17.8 |
| % Greater than 20 Micron | <1.0 | 1.2 | <1.0 | 4.4 | 6.7 | 8.0 |
| % Greater than 25 Micron | <1.0 | <1.0 | <1.0 | 2.1 | 4.7 | 3.7 |
| Helium Density ($gm^{-3}$) | NM | 2.1168 | 2.1289 | 2.1025 | 2.0482 | 2.1004 |

Note:
NM = Not measured
Ac = alpha cristobalite

TABLE V

| EXAMPLES | BET SURFACE AREA ($m^2/g$) | OIL ABSORPTION ($cm^3/100$ g) | APPARENT REFRACTIVE INDEX | WEIGHT MEAN PARTICLE SIZE (μm) | PLASTICS ABRASION VALUE | X-RAY PHASE AFTER FIRING @ 1100° C. |
| --- | --- | --- | --- | --- | --- | --- |
| EP-A-0139754 EXAMPLE 1 | 24 | 160 | 1.438 | 16.0 | 8 | AMORPHOUS |
| EP-A-0139754 EXAMPLE 2 | 22 | 175 | 1.448 | 16.6 | 6 | AMORPHOUS |
| EP-A-0139754 EXAMPLE 3 | 47 | 185 | 1.437 | 16.4 | 3 | AMORPHOUS |
| OF THIS INVENTION EXAMPLE 1 | 40 | 125 | 1.441 | 8.3 | 24 | ALPHA-CRISTOBALITE |
| OF THIS INVENTION EXAMPLE 3 | 62 | 100 | 1.443 | 6.2 | 17 | ALPHA-CRISTOBALITE |
| OF THIS INVENTION EXAMPLE 5 | 76 | 90 | 1.439 | 6.5 | 21 | ALPHA-CRISTOBALITE |

TABLE VI

| Transparent Gel Toothpaste | % |
|---|---|
| Sorbosil TC15* | 10.0 |
| Silica of invention | 6.0 |
| Sodium Carboxymethyl Cellulose | 0.7 |
| Sorbitol, 70% non-crystallisable | 61.1 |
| Polyethylene Glycol 1500 | 5.0 |
| Sodium Lauryl Sulphate | 1.5 |
| Sodium Monofluoro-phosphate | 0.8 |
| Flavour | 1.0 |
| Saccharin | 0.2 |
| Colour, Blue, CI42090 | 0.015 |
| Water & Minor ingredients | to 100 |
| Properties - Initial Density g cm$^{-3}$ (25° C.) | 1.37 |

*Sorbosil TC15 is a thickening silica obtainable from Crosfield Chemicals of Warrington, England.

We claim:

1. An amorphous silica having
    (i) a B.E.T. surface area in the range from about 10 to about 90 m$^2$g$^{-1}$,
    (ii) a weight mean particle size in the range from about 5 to about 15 microns, with less than 15% of the weight particle size distribution greater than 20 microns and less than 5% greater than 25 microns,
    (iii) a plastics abrasion value in the range from about 16 to about 26,
    (iv) a transmission of at least about 70% in the refractive index range of 1.430 to 1.443,
    (v) an oil absorption in the range from about 70 to about 150.

2. Process for the preparation of an amorphous precipitated silica having
    (i) a B.E.T. surface area in the range from about 10 to about 90 m$^2$g$^{-1}$,
    (ii) a weight mean particle size in the range from about 5 to about 15 microns, with less than 15% of the weight particle size distribution greater than 20 microns and less than 5% greater than 25 microns
    (iii) a plastics abrasion value in the range from about 16 to about 26
    (iv) a transmission of at least about 70% in the refractive index range of 1.430 to 1.443
    (v) an oil absorption in the range from about 70 to about 150, by reacting an alkali (M) metal silicate solution with ratio SiO$_2$:M$_2$O in the range 3.0 to 3.5, in the presence of an electrolyte with a mineral acid such that the pH is in the range from about 8.5 to about 10 and the silica concentration at the end of the primary acid addition is from about 6.0 to about 8.0 w/w, at a temperature from about 80° to about 100° C., ageing this slurry for about 10 to 50 minutes, adding a secondary amount of dilute mineral acid until the pH is in the range 2 to 5 to ensure complete neutralisation of the alkali containing silica solution, filtering, washing and drying the product obtained.

3. The process of claim 2 wherein the electrolyte is sodium chloride where the ratio of NaCl:SiO$_2$ is between 1:12 and 1:4.

* * * * *